(12) United States Patent
Levy et al.

(10) Patent No.: US 9,101,287 B2
(45) Date of Patent: Aug. 11, 2015

(54) MULTI CAMERA ENDOSCOPE ASSEMBLY HAVING MULTIPLE WORKING CHANNELS

(75) Inventors: Avi Levy, Herzliya (IL); Moshe Levi, Gane Tikva (IL)

(73) Assignee: Endochoice Innovation Center Ltd., Caesarea (IL)

( * ) Notice: Subject to any disclaimer, the term of this patent is extended or adjusted under 35 U.S.C. 154(b) by 48 days.

(21) Appl. No.: 13/413,252

(22) Filed: Mar. 6, 2012

(65) Prior Publication Data

US 2012/0232343 A1    Sep. 13, 2012

Related U.S. Application Data

(60) Provisional application No. 61/449,746, filed on Mar. 7, 2011.

(51) Int. Cl.
*A61B 1/00* (2006.01)
*A61B 1/06* (2006.01)
*A61B 1/015* (2006.01)
*A61B 1/018* (2006.01)

(52) U.S. Cl.
CPC ........... *A61B 1/0615* (2013.01); *A61B 1/00177* (2013.01); *A61B 1/00181* (2013.01); *A61B 1/015* (2013.01); *A61B 1/018* (2013.01); *A61B 1/00091* (2013.01)

(58) Field of Classification Search
USPC ......... 600/104, 106, 107, 109–116, 153, 157, 600/158, 160–182; 356/241.1–241.6; 385/117
See application file for complete search history.

(56) References Cited

U.S. PATENT DOCUMENTS

| | | |
|---|---|---|
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,590,923 A | 5/1986 | Watanabe |
| 4,641,635 A | 2/1987 | Yabe |
| 4,699,463 A | 10/1987 | D'Amelio et al. |

(Continued)

FOREIGN PATENT DOCUMENTS

| | | |
|---|---|---|
| CN | 201108422 Y | 9/2008 |
| DE | 102005008153 A1 | 11/2005 |

(Continued)

OTHER PUBLICATIONS

International Search Report for PCT/EP2009/066726, Aug. 16, 2010.

(Continued)

*Primary Examiner* — Ryan Henderson
(74) *Attorney, Agent, or Firm* — Novel IP

(57) ABSTRACT

There is provided herein an endoscope assembly, the assembly comprising at least one front-pointing camera and at least one front illuminator associated therewith, at least one side-pointing camera and at least one of side illuminator associated therewith, a first front working channel configured for insertion of a medical tool and a second front working channel configured for insertion of a medical tool.

24 Claims, 5 Drawing Sheets

(56) References Cited

U.S. PATENT DOCUMENTS

| | | |
|---|---|---|
| 4,708,126 A | 11/1987 | Toda |
| 4,736,732 A | 4/1988 | Shimonaka |
| 4,753,222 A | 6/1988 | Morishita |
| 4,794,913 A | 1/1989 | Shimonaka |
| 4,841,952 A | 6/1989 | Sato |
| 4,846,154 A | 7/1989 | MacAnally |
| 4,878,485 A | 11/1989 | Adair |
| 4,888,639 A | 12/1989 | Yabe |
| 4,905,670 A | 3/1990 | Adair |
| 4,914,521 A | 4/1990 | Adair |
| 4,974,075 A | 11/1990 | Nakajima |
| 4,982,724 A | 1/1991 | Saito |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,550,582 A | 8/1996 | Takasugi |
| 5,585,840 A | 12/1996 | Watanabe |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,852,511 A | 12/1998 | Tateyama |
| 5,871,439 A | 2/1999 | Takahashi |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A * | 8/1999 | Kimura .................. 348/294 |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,184,923 B1 | 2/2001 | Miyazaki |
| 6,185,046 B1 | 2/2001 | Togino |
| 6,201,646 B1 | 3/2001 | Togino |
| 6,201,648 B1 | 3/2001 | Togino |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |

(56) References Cited

U.S. PATENT DOCUMENTS

| | | |
|---|---|---|
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 * | 12/2004 | Stelzer et al. ............ 600/106 |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |

(56) References Cited

U.S. PATENT DOCUMENTS

| | | | |
|---|---|---|---|
| 7,725,013 | B2 | 5/2010 | Sugimoto |
| 7,728,867 | B2 | 6/2010 | Fukuyama |
| 7,734,160 | B2 | 6/2010 | Sudo |
| 7,746,566 | B2 | 6/2010 | Mizusawa |
| 7,749,156 | B2 | 7/2010 | Ouchi |
| 7,749,159 | B2 | 7/2010 | Crowley |
| 7,758,495 | B2 | 7/2010 | Pease |
| 7,758,499 | B2 | 7/2010 | Adler |
| 7,772,786 | B2 | 8/2010 | Hosoda |
| 7,773,110 | B2 | 8/2010 | Abe |
| 7,773,122 | B2 | 8/2010 | Irion |
| 7,773,318 | B2 | 8/2010 | Takato |
| 7,775,971 | B2 | 8/2010 | Fujimori |
| 7,775,973 | B2 | 8/2010 | Okada |
| 7,789,822 | B2 | 9/2010 | Suzuki |
| 7,800,656 | B2 | 9/2010 | Takeuchi |
| RE41,807 | E | 10/2010 | Yokoi |
| 7,821,529 | B2 | 10/2010 | Mochida |
| 7,837,614 | B2 | 11/2010 | Segawa |
| 7,841,880 | B2 | 11/2010 | Ikeda |
| 7,846,090 | B2 | 12/2010 | Pilvisto |
| 7,852,513 | B2 | 12/2010 | Donomae |
| 7,893,956 | B2 | 2/2011 | Ayrenschmalz |
| 7,896,802 | B2 | 3/2011 | Otawara |
| 7,901,352 | B2 | 3/2011 | Minami |
| 7,907,168 | B2 | 3/2011 | Eino |
| 7,907,170 | B2 | 3/2011 | Watanabe |
| 7,907,352 | B2 | 3/2011 | Miyano |
| 7,914,443 | B2 | 3/2011 | Uchimura |
| 7,918,788 | B2 | 4/2011 | Lin |
| 7,938,773 | B2 | 5/2011 | Kawai |
| 7,940,296 | B2 | 5/2011 | Ogino |
| 7,942,814 | B2 | 5/2011 | Remijan |
| 7,951,068 | B2 | 5/2011 | Kura |
| 7,967,745 | B2 | 6/2011 | Gilad |
| 7,976,462 | B2 | 7/2011 | Wright |
| 7,995,093 | B2 | 8/2011 | Takeuchi |
| 7,998,064 | B2 | 8/2011 | Otawara |
| 8,002,696 | B2 | 8/2011 | Suzuki |
| 8,027,101 | B2 | 9/2011 | Suda |
| 8,033,992 | B2 | 10/2011 | Hino |
| 8,035,684 | B2 | 10/2011 | Wakito |
| 8,038,600 | B2 | 10/2011 | Uchiyama |
| 8,043,207 | B2 | 10/2011 | Adams |
| 8,060,172 | B2 | 11/2011 | Ishihara |
| 8,063,962 | B2 | 11/2011 | Hagihara |
| 8,066,631 | B2 | 11/2011 | Wimmer |
| 8,072,483 | B2 | 12/2011 | Tomioka |
| 8,072,537 | B2 | 12/2011 | Schwarz |
| 8,072,693 | B2 | 12/2011 | Togino |
| 8,075,477 | B2 | 12/2011 | Nakamura |
| 8,075,478 | B2 | 12/2011 | Campos |
| 8,098,441 | B2 | 1/2012 | Sasamoto |
| 8,100,920 | B2 | 1/2012 | Gambale |
| 8,102,415 | B2 | 1/2012 | Iriyama |
| 8,105,233 | B2 | 1/2012 | AbouElKheir |
| 8,113,846 | B2 | 2/2012 | Wallaker |
| 8,125,514 | B2 | 2/2012 | Sekiguchi |
| 8,125,515 | B2 | 2/2012 | Hibi |
| 8,130,454 | B2 | 3/2012 | Noguchi |
| 8,135,192 | B2 | 3/2012 | Matsuzaki |
| 8,135,454 | B2 | 3/2012 | Daniels |
| 8,139,296 | B2 | 3/2012 | Ito |
| 8,144,191 | B2 | 3/2012 | Kawanishi |
| 8,149,274 | B2 | 4/2012 | Yamazaki |
| 8,152,718 | B2 | 4/2012 | Cheng |
| 8,152,821 | B2 | 4/2012 | Gambale |
| 8,157,798 | B2 | 4/2012 | Takahashi |
| 8,164,836 | B2 | 4/2012 | Uzawa |
| 8,167,791 | B2 | 5/2012 | Tanaka |
| 8,167,795 | B2 | 5/2012 | Hoeg |
| 8,167,796 | B2 | 5/2012 | Negishi |
| 8,182,419 | B2 | 5/2012 | Kohno |
| 8,187,171 | B2 | 5/2012 | Irion |
| 8,187,174 | B2 | 5/2012 | Wang |
| 8,189,041 | B2 | 5/2012 | Konishi |
| 8,189,062 | B2 | 5/2012 | Irion |
| 8,194,380 | B2 | 6/2012 | Murata |
| 8,197,400 | B2 | 6/2012 | Boutillette |
| 8,200,042 | B2 | 6/2012 | Doi |
| 8,208,015 | B2 | 6/2012 | Unsai |
| 8,211,009 | B2 | 7/2012 | Tanaka |
| 8,212,862 | B2 | 7/2012 | Kase |
| 8,212,863 | B2 | 7/2012 | Tanaka |
| 8,221,309 | B2 | 7/2012 | Iida |
| 8,221,311 | B2 | 7/2012 | Campos |
| 8,223,198 | B2 | 7/2012 | Shibasaki |
| 8,228,369 | B2 | 7/2012 | Kojima |
| 8,229,549 | B2 | 7/2012 | Whitman |
| 8,235,942 | B2 | 8/2012 | Frassica |
| 8,248,414 | B2 | 8/2012 | Gattani |
| 8,262,565 | B2 | 9/2012 | Okada |
| 8,279,275 | B2 | 10/2012 | Gono |
| 8,295,566 | B2 | 10/2012 | Nishimura |
| 8,310,529 | B2 | 11/2012 | Krupnick |
| 8,334,900 | B2 | 12/2012 | Qu |
| 8,345,092 | B2 | 1/2013 | Takasaki |
| 8,348,835 | B2 | 1/2013 | Fujimori |
| 8,360,960 | B2 | 1/2013 | Sasaki |
| 8,360,964 | B2 | 1/2013 | Ertas |
| 8,366,623 | B2 | 2/2013 | Misono |
| 8,382,673 | B2 | 2/2013 | Nagano |
| 8,394,013 | B2 | 3/2013 | Ichimura |
| 8,394,014 | B2 | 3/2013 | Fuerst |
| 8,425,405 | B2 | 4/2013 | Mitani |
| 8,435,173 | B2 | 5/2013 | Hosaka |
| 8,439,829 | B2 | 5/2013 | Miyamoto |
| 8,444,547 | B2 | 5/2013 | Miyamoto |
| 8,444,548 | B2 | 5/2013 | Kumei |
| 8,449,456 | B2 | 5/2013 | Ueno |
| 8,449,457 | B2 | 5/2013 | Aizenfeld |
| 8,456,562 | B2 | 6/2013 | Ishii |
| 8,460,182 | B2 | 6/2013 | Ouyang |
| 8,465,421 | B2 | 6/2013 | Finkman |
| 8,480,670 | B2 | 7/2013 | Sugita |
| 8,491,467 | B2 | 7/2013 | Miyamoto |
| 8,520,919 | B2 | 8/2013 | Stepp |
| 8,523,764 | B2 | 9/2013 | Hatcher |
| 8,523,766 | B2 | 9/2013 | Kudoh |
| 2002/0007110 | A1 | 1/2002 | Irion |
| 2002/0087047 | A1 | 7/2002 | Remijan |
| 2002/0098732 | A1 | 7/2002 | Shimizu |
| 2002/0109774 | A1 | 8/2002 | Meron |
| 2002/0151768 | A1 | 10/2002 | Akiba |
| 2002/0161282 | A1 | 10/2002 | Fulghum |
| 2002/0183591 | A1 | 12/2002 | Matsuura |
| 2003/0032860 | A1 | 2/2003 | Avni |
| 2003/0036681 | A1 | 2/2003 | Aviv |
| 2003/0055314 | A1 | 3/2003 | Petitto |
| 2003/0125788 | A1 | 7/2003 | Long |
| 2003/0130564 | A1 | 7/2003 | Martone |
| 2003/0139648 | A1 | 7/2003 | Foley |
| 2003/0158462 | A1 | 8/2003 | Takase |
| 2003/0181787 | A1 | 9/2003 | Kondo |
| 2003/0199860 | A1 | 10/2003 | Loeb |
| 2004/0015049 | A1 | 1/2004 | Zaar |
| 2004/0019347 | A1 | 1/2004 | Sakurai |
| 2004/0024290 | A1 | 2/2004 | Root |
| 2004/0034311 | A1 | 2/2004 | Mihalcik |
| 2004/0073120 | A1 | 4/2004 | Motz |
| 2004/0104999 | A1 | 6/2004 | Okada |
| 2004/0111012 | A1 | 6/2004 | Whitman |
| 2004/0133076 | A1 | 7/2004 | Kobayashi |
| 2004/0143162 | A1 | 7/2004 | Krattiger |
| 2004/0158129 | A1* | 8/2004 | Okada et al. .................. 600/168 |
| 2004/0160682 | A1 | 8/2004 | Miyano |
| 2004/0176661 | A1 | 9/2004 | Futatsugi |
| 2004/0210113 | A1 | 10/2004 | Hasegawa |
| 2004/0220451 | A1 | 11/2004 | Gravenstein |
| 2004/0242958 | A1 | 12/2004 | Fujikawa |
| 2004/0242961 | A1 | 12/2004 | Bughici |
| 2004/0254423 | A1 | 12/2004 | Wendlandt |
| 2004/0267093 | A1 | 12/2004 | Miyagi |
| 2005/0020876 | A1 | 1/2005 | Shioda |

(56) References Cited

U.S. PATENT DOCUMENTS

| | | |
|---|---|---|
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1* | 4/2005 | Okada et al. .................. 600/104 |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0261553 A1 | 11/2005 | Swain |
| 2005/0272975 A1 | 12/2005 | McWeeney |
| 2005/0284491 A1 | 12/2005 | Tashiro |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1* | 7/2006 | Watts et al. .................. 600/113 |
| 2006/0173244 A1 | 8/2006 | Boulais |
| 2006/0183971 A1 | 8/2006 | Haviv |
| 2006/0183975 A1* | 8/2006 | Saadat et al. .................. 600/139 |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1* | 3/2008 | Larkin et al. .................. 606/130 |
| 2008/0100699 A1 | 5/2008 | Hibi |
| 2008/0130108 A1 | 6/2008 | Bayer |
| 2008/0139881 A1 | 6/2008 | Cover |
| 2008/0167529 A1* | 7/2008 | Otawara .................. 600/168 |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0054790 A1 | 2/2009 | Czaniera |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0016673 A1* | 1/2010 | Bandy et al. .................. 600/178 |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0249496 A1 | 9/2010 | Cardenas |
| 2010/0256447 A1 | 10/2010 | Dubi |
| 2010/0286475 A1 | 11/2010 | Robertson |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1 | 3/2011 | Cushner |

(56) References Cited

U.S. PATENT DOCUMENTS

| | | |
|---|---|---|
| 2011/0112363 A1 | 5/2011 | Koga |
| 2011/0160530 A1 | 6/2011 | Ratnakar |
| 2011/0184243 A1 | 7/2011 | Wright |
| 2011/0196200 A1 | 8/2011 | Glozman |
| 2011/0196204 A1 | 8/2011 | Setty |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0314521 A1 | 11/2013 | Satake |
| 2013/0317295 A1 | 11/2013 | Morse |

FOREIGN PATENT DOCUMENTS

| | | | | |
|---|---|---|---|---|
| EP | 0029555 | A2 | 6/1981 | |
| EP | 543738 | A1 | 5/1993 | |
| EP | 730844 | | 9/1996 | |
| EP | 1195630 | A2 | 4/2002 | |
| EP | 1325458 | | 7/2003 | |
| EP | 1347702 | A2 | 10/2003 | |
| EP | 948283 | B1 | 4/2004 | |
| EP | 1535565 | | 6/2005 | |
| EP | 1073365 | B1 | 7/2005 | |
| EP | 1627595 | A1 | 2/2006 | |
| EP | 668738 | B1 | 6/2006 | |
| EP | 1472972 | B1 | 10/2006 | |
| EP | 1790280 | A1 | 5/2007 | |
| EP | 1834572 | A1 | 9/2007 | |
| EP | 1952750 | | 8/2008 | |
| EP | 1977675 | | 10/2008 | |
| EP | 1977682 | A2 | 10/2008 | |
| EP | 1974000653 | | 10/2008 | |
| EP | 1992292 | A1 | 11/2008 | |
| EP | 2022389 | A1 | 2/2009 | |
| EP | 2144571 | A2 | 1/2010 | |
| EP | 2276389 | A1 | 1/2011 | |
| EP | 1835847 | B1 | 5/2011 | |
| EP | 1870014 | B1 | 1/2012 | |
| EP | 2501271 | A1 | 9/2012 | |
| EP | 2503933 | A1 | 10/2012 | |
| EP | 2512577 | A2 | 10/2012 | |
| EP | 2529660 | A1 | 12/2012 | |
| EP | 2596756 | A1 | 5/2013 | |
| EP | 2623019 | A1 | 8/2013 | |
| GB | 2352922 | A | 2/2001 | |
| JP | 55078932 | | 6/1980 | |
| JP | 61055657 | | 11/1986 | |
| JP | 5049000594 | | 3/1993 | |
| JP | 6105000800 | | 4/1994 | |
| JP | 7000000352 | | 1/1995 | |
| JP | 8122000657 | | 5/1996 | |
| JP | 1013007179 | | 4/1998 | |
| JP | 1015001113 | | 6/1998 | |
| JP | 11137512 | A * | 5/1999 | ............... A61B 1/00 |
| JP | 1116009340 | | 6/1999 | |
| JP | 1116009341 | | 6/1999 | |
| JP | 2000171727 | A | 6/2000 | |
| JP | 2001061762 | | 3/2001 | |
| JP | 2001198086 | | 7/2001 | |
| JP | 2002000559 | | 1/2002 | |
| JP | 2002058636 | | 2/2002 | |
| JP | 2002065575 | | 3/2002 | |
| JP | 2002078675 | | 3/2002 | |
| JP | 2002216902 | | 8/2002 | |
| JP | 2003038431 | | 2/2003 | |
| JP | 2003061900 | | 3/2003 | |
| JP | 2003111724 | | 4/2003 | |
| JP | 2003190082 | | 7/2003 | |
| JP | 2003220017 | | 8/2003 | |
| JP | 2003245247 | | 9/2003 | |
| JP | 2004022391 | | 1/2004 | |
| JP | 2004049754 | | 2/2004 | |
| JP | 2004049756 | | 2/2004 | |
| JP | 2004129834 | | 4/2004 | |
| JP | 2005013557 | A | 1/2005 | |
| JP | 2005058547 | | 3/2005 | |
| JP | 2005253543 | A * | 9/2005 | ............... A61B 1/00 |
| JP | 2006068109 | A | 3/2006 | |
| JP | 2006218155 | | 8/2006 | |
| JP | 2007020866 | A | 2/2007 | |
| JP | 2007185276 | | 7/2007 | |
| JP | 2008161569 | A | 7/2008 | |
| JP | 2008229204 | | 10/2008 | |
| JP | 2009233186 | | 10/2009 | |
| JP | 2010178766 | A | 8/2010 | |
| JP | 2010178766 | A * | 8/2010 | ............... A61B 1/00 |
| WO | 9219148 | A1 | 11/1992 | |
| WO | 0052643 | A1 | 9/2000 | |
| WO | 0245595 | | 6/2002 | |
| WO | 2004026125 | | 4/2004 | |
| WO | 2005082228 | A1 | 9/2005 | |
| WO | 2006073581 | | 7/2006 | |
| WO | 2006105932 | A1 | 10/2006 | |
| WO | 2007113801 | A2 | 10/2007 | |
| WO | 2007136859 | A2 | 11/2007 | |
| WO | 2008012813 | A1 | 1/2008 | |
| WO | 2008073243 | | 6/2008 | |
| WO | 2008093288 | | 8/2008 | |
| WO | 2008139770 | | 11/2008 | |
| WO | 2008155776 | | 12/2008 | |
| WO | 2008156623 | | 12/2008 | |

(56) References Cited

FOREIGN PATENT DOCUMENTS

| | | |
|---|---|---|
| WO | 2009009414 | 1/2009 |
| WO | 2009025843 | 2/2009 |
| WO | 2009040744 | 4/2009 |
| WO | 2009095915 | 8/2009 |
| WO | 2010028612 | 3/2010 |
| WO | 2010045406 | 4/2010 |
| WO | 2010066788 | 6/2010 |
| WO | 201014658 A1 | 12/2010 |
| WO | 2011008922 | 1/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2014061023 | 4/2014 |

OTHER PUBLICATIONS

Brochure for US Endoscopy's AquaShield Water Bottle System, 2010.
Office Action dated Feb. 27, 2014 for U.S. Appl. No. 13/557,114.
Office Action dated May 30, 2014 for U.S. Appl. No. 13/119,032.
Office Action dated May 27, 2014 for U.S. Appl. No. 13/212,627.
Office Action dated May 9, 2014 for U.S. Appl. No. 13/413,059.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.
International Search Report of PCT/IL10/00476 mailed Sep. 27, 2010, 2 pages.
International Search Report of PCT/IL2011/000745, dated May 8, 2012.
Office Action dated Apr. 3, 2014 for U.S. Appl. No. 13/413,141.
Office Action dated Feb. 24, 2014 for U.S. Appl. No. 13/190,968.
Office Action dated Jul. 1, 2014 for U.S. Appl. No. 13/655,120.
Office Action dated Jul. 31, 2014 for U.S. Appl. No. 13/713,449.
Office Action dated Jun. 12, 2014 for U.S. Appl. No. 13/713,466.

* cited by examiner

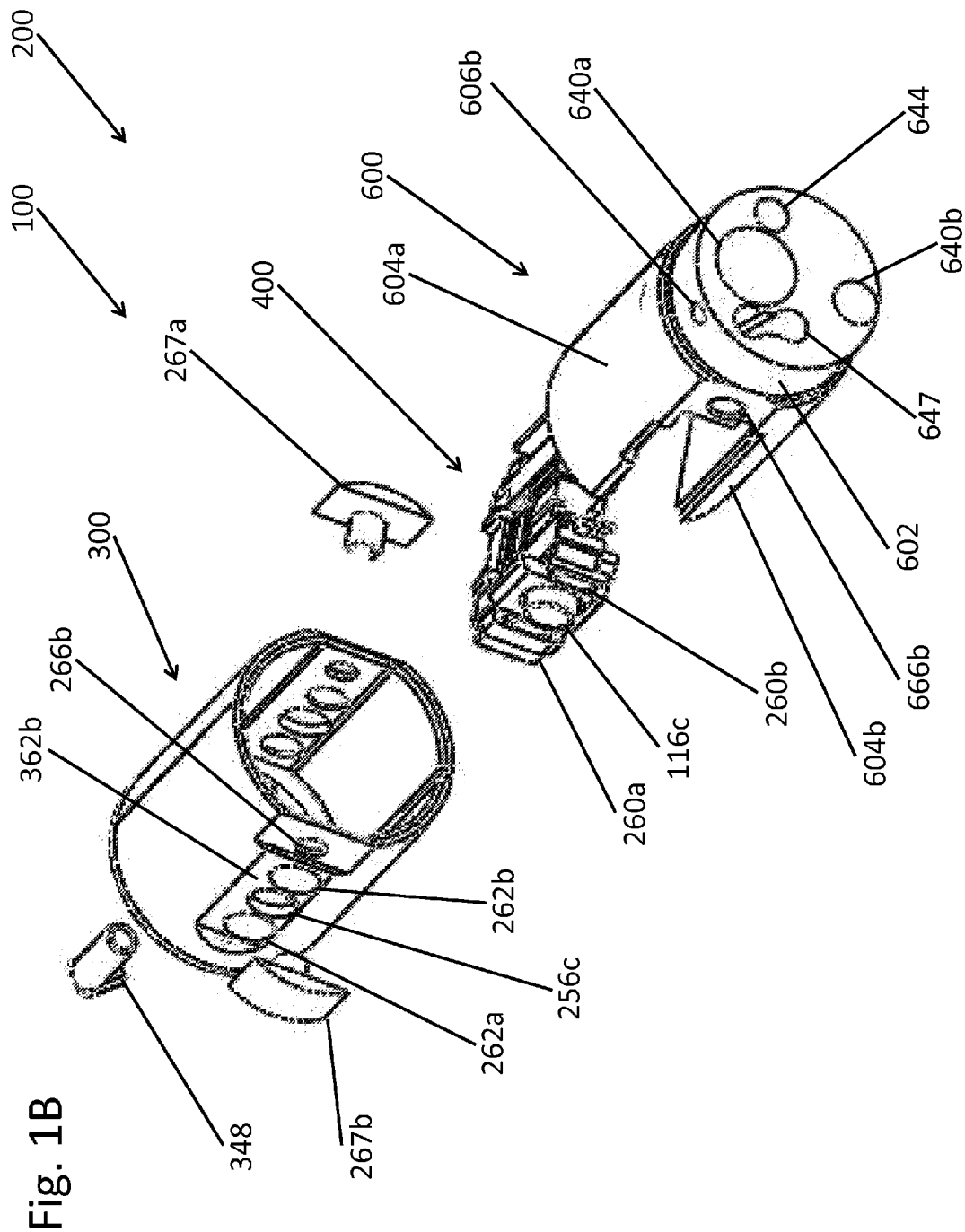

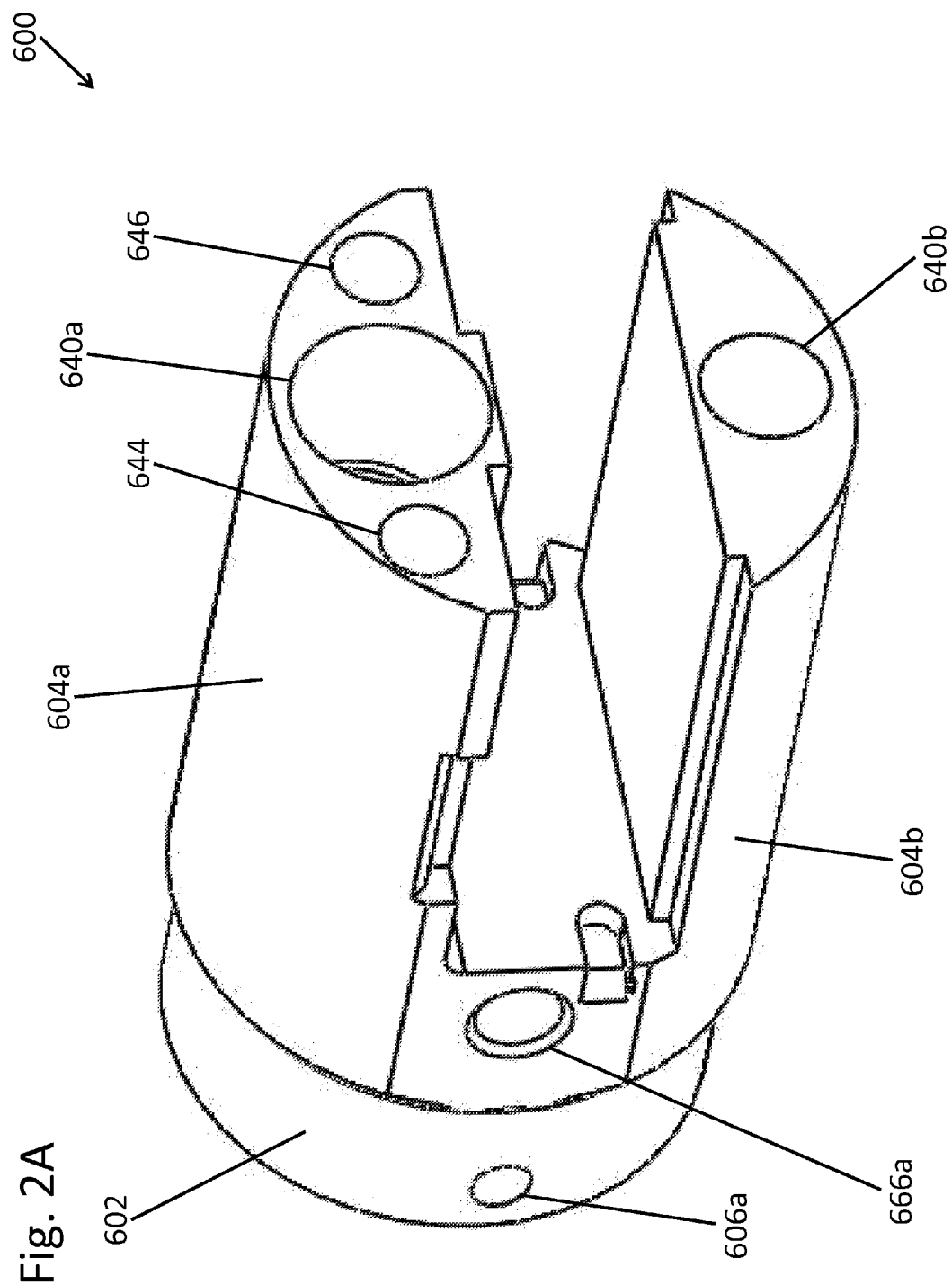

MULTI CAMERA ENDOSCOPE ASSEMBLY HAVING MULTIPLE WORKING CHANNELS

REFERENCE TO CO-PENDING APPLICATIONS

Priority is claimed to U.S. Provisional Patent application Ser. No. 61/449,746, filed on Mar. 7, 2011.

FIELD OF THE INVENTION

Embodiments of the invention relate to a multi camera endoscope assembly having two or more working channels.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various medical tools may be inserted through a working channel in the endoscope for performing different medical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of medical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

One of the disadvantages of such endoscopes, is their limited access they provide to medical tools, limited field of view and their complicated packing of all the required elements, such as electronics and fiber optics together with fluid carrying elements in the small sized endoscope tip section.

There is thus a need in the art for endoscopes, such as colonoscopies, that allow a broader field of view and allow extended access of medical tools as well as enabling efficient packing of all necessary elements in the tip section, while maintaining their function.

SUMMARY

The following embodiments and aspects thereof are described and illustrated in conjunction with systems, tools and methods, which are meant to be exemplary and illustrative, not limiting in scope.

There is provided herein, according to some embodiments of the invention an endoscope assembly, the assembly comprising: at least one front-pointing camera and at least one front illuminator associated therewith; at least one side-pointing camera and at least one of side illuminator associated therewith; a first front working channel configured for insertion of a medical tool; and a second front working channel configured for insertion of a medical tool.

In some embodiments, the assembly further comprises at least one front fluid injector configured for cleaning at least one of the front-pointing camera and at least one of the front illuminator.

In some embodiments, the assembly further comprises at least one side fluid injector configured for cleaning at least one of the side-pointing camera and at least one of the side illuminator.

In some embodiments, the assembly further comprises a pathway fluid injector for inflating and/or cleaning a body cavity into which the endoscope is inserted.

In some embodiments, the assembly further comprises two side-pointing cameras.

In some embodiments, each of the side-pointing cameras is directed to opposing sides.

In some embodiments, each of the side-pointing cameras is essentially perpendicular to the front camera surface.

In some embodiments, the at least one side-pointing camera forms an obtuse angle with the front camera surface In some embodiments, the at least one side-pointing camera is forming an acute angle with the front camera surface In some embodiments, at least one of the front and side illuminators comprises at least one discrete illuminator.

In some embodiments, each of the front and side illuminators comprises a light-emitting diode (LED).

In some embodiments, at least one of the front and side illuminators is configured to emit white light.

In some embodiments, at least one of the front and side illuminators is configured to emit ultraviolet light.

In some embodiments, at least one of the front and side illuminators is configured to emit infrared light.

In some embodiments, at least one of the front and side illuminators is configured to emit near-infrared light.

In some embodiments, the front and side illuminators are configured to emit light in different wavelengths.

In some embodiments, each of the front-pointing camera and the side-pointing camera comprises an image sensor such as, but not limited to, a Charge Coupled Device (CCD) or a Complementary Metal Oxide Semiconductor (CMOS).

In some embodiments, the front and side fluid injectors are connected to a same fluid supply channel.

In some embodiments, the endoscope is a colonoscope. In some embodiments, the endoscope is a flexible endoscope. In some embodiments, the endoscope is a gastroscope.

In some embodiments, fields of view of the front-pointing camera and side-pointing camera are at least partially overlapping.

In some embodiments, at least one of the front and side cameras comprises a lens assembly providing a field of view of 90 degrees or more.

In some embodiments, at least one of the front and side cameras comprises a lens assembly providing a field of view of 120 degrees or more.

In some embodiments, at least one of the front and side cameras comprises a lens assembly providing a focal length of approximately 3-100 millimeters.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 1B shows an exploded view of a tip section of an endoscope assembly according to some embodiments;

FIG. 2A shows a perspective view of a fluid channeling component of an endoscope assembly according to some embodiments;

DETAILED DESCRIPTION

Figure 1A:
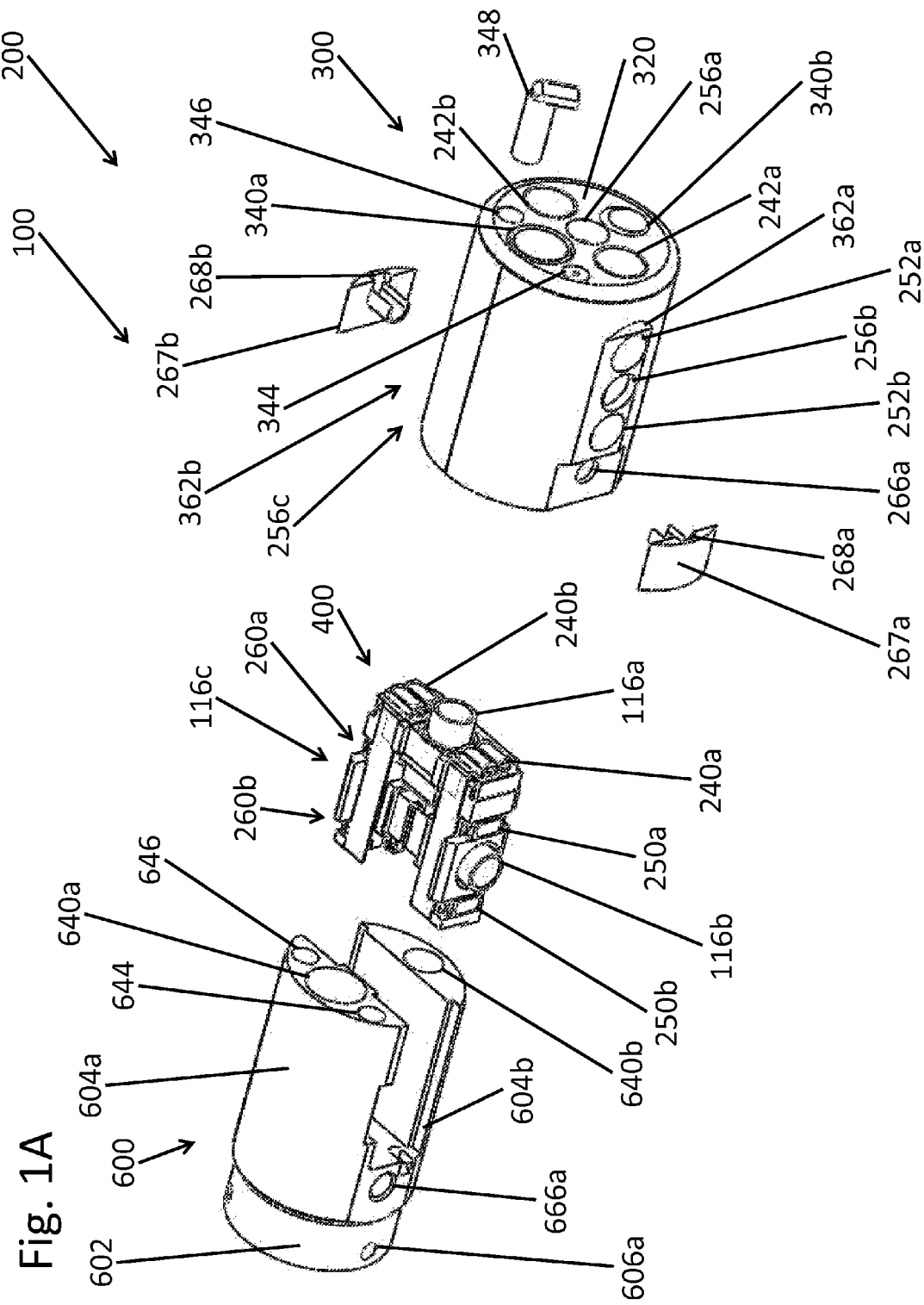
FIG. 1A shows an exploded view of a tip section of an endoscope assembly according to some embodiments.

Reference is now made to FIGS. 1A and 1B, which show exploded views of a tip section 200 of an endoscope assembly 100 according to an embodiment.

An aspect of some embodiments relates to an endoscope assembly 100 having a tip section 200 equipped with two or more front working channels.

It is noted that the term "endoscope" as mentioned herein may refer particularly to a colonoscope, according to some embodiments, but is not limited only to colonoscopes. The term "endoscope" may refer to any instrument used to examine the interior of a hollow organ or cavity of the body.

It is noted that the term "multi" or "multiple" as mentioned herein may refer to two or more, for example, three, four, five or more.

Tip section 200 may be turnable by way of flexible shaft (not shown) which may also be referred to as a bending section, for example a vertebra mechanism.

According to some embodiments, tip section 200 of an endoscope may include a tip cover 300, an electronic circuit board assembly 400 and a fluid channeling component 600.

Electronic circuit board assembly 400 may be configured to carry a front-pointing camera 116a and two side-pointing cameras 116b, 116c which may be similar to front-pointing camera 116a and may include a Charge Coupled Device (CCD) or a Complementary Metal Oxide Semiconductor (CMOS) image sensor.

According to some embodiments, side-pointing cameras 116b and 116c may be installed such that their field of views are substantially opposing. However, different configurations and number of side-pointing cameras are possible within the general scope of the current invention.

Electronic circuit board assembly 400 may be configured to carry front illuminators 240a, 240b, which may be associated with front-pointing camera 116a, may be positioned to essentially illuminate front-pointing camera's 116a fields of view.

In addition, electronic circuit board assembly 400 may be configured to carry side illuminators 250a, 250b, which may be associated with side-pointing camera 116b and may be positioned to essentially illuminate side-pointing cameras' 116b and side illuminators 260a, 260b, which may be associated with side-pointing camera 116c and may be positioned to essentially illuminate side-pointing cameras' 116c.

Front illuminators 240a, 240b and side illuminators 250a, 250b, 260a and 260b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally—in contrast to a non-discrete illuminator, which may be, for example, a fiber optic merely transmitting light generated remotely.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a front optical assembly 256a of front-pointing camera 116a. Front optical assembly 256a may include a plurality of lenses, static or movable, which may provide a field of view of up to essentially 180 degrees. Front optical assembly 256a may provide a focal length of up to about 100 millimeters.

Optical axis of front-pointing camera 116a may be essentially directed along the long dimension of the endoscope. However, since front-pointing camera 116a is typically a wide angle camera, its field of view may include viewing directions at large angles to its optical axis. Additionally, front panel 320 may include optical windows 242a and 242b of illuminators 240a and 240b, respectively. It should be noted that number of illumination sources used for illumination of the field of view may vary.

In addition, front panel 320 may include a working channel opening 340a of a working channel 640a, and a second working channel opening 340b of a second working channel 640b which are further discussed below.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646 having a nozzle 348 aimed at front optical assembly 256a.

Injector channel 646 may be fed by a fluid or fluid blend such as water and/or gas and configured for injecting fluid blend (liquid and/or gas) to wash contaminants such as blood, feces and other debris from front optical assembly 256a of front-pointing camera 116a. In addition, the fluid blend may include gas, which may be used for inflating a body cavity.

Optionally, injector channel 646 may be configured for cleaning front optical assembly 256a and one, two or all of optical windows 242a and 242b.

A sidewall 362a of tip cover 300 may include an optical assembly 256b for side-pointing camera 116b, which may be similar to front optical assembly 256a and optical windows 252a and 252b of illuminators 250a and 250b for side-pointing camera 116b.

A sidewall 362b of tip cover 300, which may be similar to sidewall 362a and located on the opposite side of tip cover 300, may include an optical assembly 256c for side-pointing camera 116c, which may be similar to front optical assembly 256a and optical windows 262a and 262b of illuminators 260a and 260b for side-pointing camera 116b.

Optical axis of side-pointing cameras 116b and 116c may be essentially directed perpendicular to the long dimension of the endoscope. However, since side-pointing cameras 116b and 116c are typically a wide angle camera, its field of view may include viewing directions at large angles to its optical axis.

According to some embodiments, side injector channels 666a and 666b may be configured to supply fluids for cleaning any of the tip elements (such as any optical assembly, windows, illuminators, and other elements). Side injectors opening 266a and 266b of side injector channels 666a and 666b may be located at distal end of sidewalls 362a and 362b respectively. Nozzle covers 267a and 267b may be configured to fit side injectors opening 266a and 266b.

Additionally, nozzle covers 267a and 267b may include nozzles 268a and 268b which may be aimed at side optical assembly 256b and 256c and configured for injecting a fluid or fluid blend to wash contaminants such as blood, feces and other debris from side optical assembly 256b and 256c of side-pointing camera 116b and 116c. Optionally, nozzles 268a and 268b may be configured for cleaning side optical assembly 256b and 256c and optical windows 252a, 252b, 262b and/or 262b.

Optionally, injector channel 646 and side injector channels 666a and 666b may be fed from same channel.

It is noted that according to some embodiments, the endoscope tip may include more than one optical window and illuminators on the side and more than one optical window and illuminators on the front.

Sidewalls 362a and 362b may have a form of an essentially flat surface, which assists in directing the cleaning fluid injected from injector channel 666a and 666b towards side optical assembly 256b and 256c and optical windows 252a, 252b, 262a and/or 262b. Lack of such flat surface may result in dripping of the cleaning fluid along the curved surface of tip section 200 of the endoscope without performing the desired cleaning action.

Figure 2B:
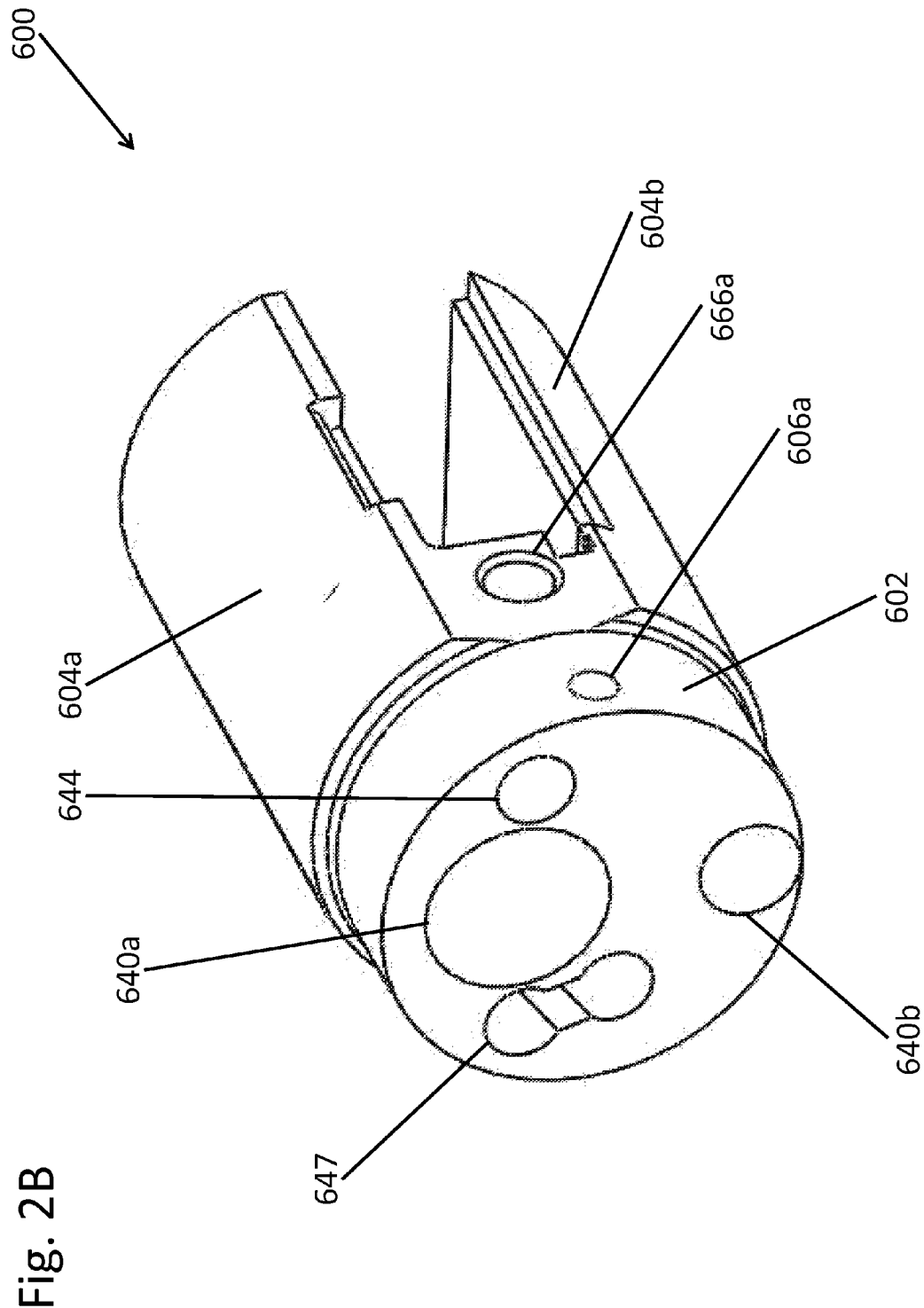
FIG. 2B shows a perspective view of a fluid channeling component of an endoscope assembly according to some embodiments.
Figure 2C:
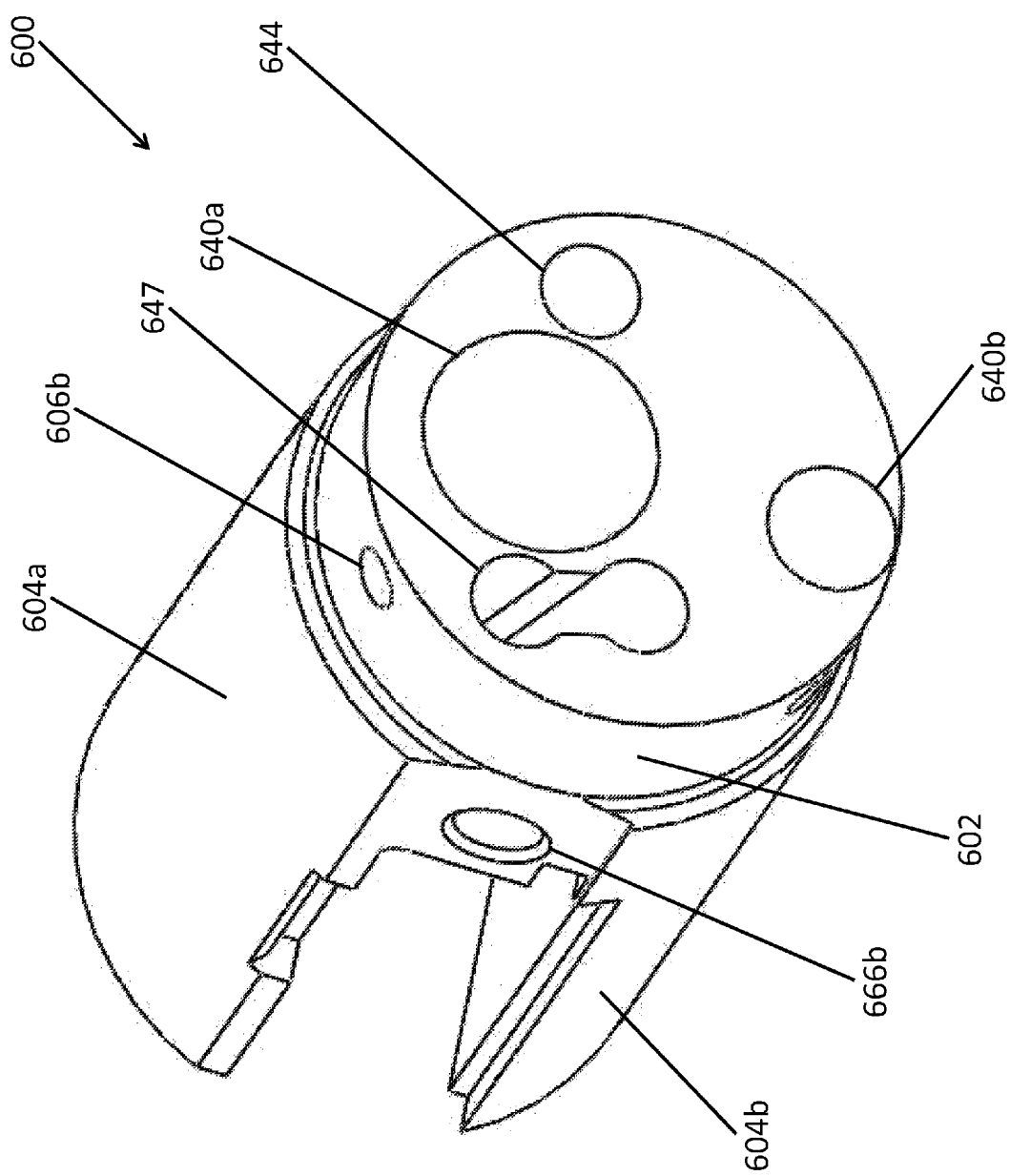
FIG. 2C shows a perspective view of a fluid channeling component of an endoscope assembly according to some embodiments.

Reference is now made to FIGS. 2A, 2B and 2C which show a perspective views of a fluid channeling component 600 of an endoscope assembly 100 according to an embodiment.

According to some embodiments, fluid channeling component 600 may be configured as a separate component from electronic circuit board assembly 400 (FIG. 1). This configuration may be adapted to separate the fluid channels and working channels 640a and 640b, which are located in fluid channeling component 600 from the sensitive electronic and optical parts which may be located in the area of electronic circuit board assembly 400 (FIG. 1).

According to some embodiments, fluid channeling component 600 may include a Proximal fluid channeling section 602 which may have an essentially cylindrical shape, a primary distal channeling section 604a and a secondary distal channeling section 604b. Primary distal fluid channeling section 604a and secondary distal channeling section 604b may partially continue the cylindrical shape of proximal fluid channeling section 602 and may have a shape of a partial cylinder (optionally elongated partial cylinder). Primary distal fluid channeling section 604a and secondary distal channeling section 604b may form solely two parallel fractions of the cylinder (along the height axis of the cylinder), wherein the third fraction of the cylinder (along the height axis of the cylinder) is missing. Primary distal fluid channeling section 604a and secondary distal channeling section 604b may be integrally formed as a unitary block with proximal fluid channeling section 602. The height of primary distal fluid channeling section 604a and secondary distal channeling section 604b may by higher than that of proximal fluid channeling section 602. In the case of primary distal fluid channeling section 604a and secondary distal channeling section 604b may have the shape of the partial cylinder (for example, partial cylinder having only a fraction of a cylinder shape along one side of the height axis) and provide a space to accommodate electronic circuit board assembly 400 (FIG. 1).

Proximal fluid channeling section 602 may include integrated screw nuts 606a and 606b, which may be configured for securing tip section 200 (FIG. 1) to the endoscope shaft (not shown).

Reference is now made back to FIGS. 1A and 1B. Tip section 200 may include a front-pointing camera 116a as well as side-pointing cameras 116b and 116c. While front-pointing camera 116a may be able to detect objects of interest (such as a polyp or another pathology), based on front-pointing camera's 116a field of view, side-pointing camera may be able to detect additional objects of interest which are normally hidden from the front-pointing camera 116a.

Reference is now made back to FIGS. 2A, 2B and 2C. Primary distal fluid channeling section 604a may include working channel 640a having a working channel openings 340a, which may be configured for insertion of a medical (such as a surgical) tool, for example, to remove, treat and/or extract a sample of the object of interest found in the colon or its entirety for biopsy.

Working channel 640a may be formed as an essentially cylindrical channel located within primary distal channeling section 604a along the long dimension of the endoscope and placed in parallel to primary distal fluid channeling section 604a.

Once an object of interest has been detected, endoscope operator may desire to insert one or more medical tools and remove, treat and/or extract a sample of the polyp or its entirety for biopsy. Therefore, it may be beneficial for the endoscope's operator to be able to use more than one medical tool.

Advantageously, secondary distal channeling section 604b may include a second working channels 640b having a working channel opening 340b which may be similar to working channel 640a and may be configured for insertion of a medical tool, for example but not necessarily, in addition to the medical tool which may be inserted through working channel 640a. The operator may also choose from which working channel he or she would like to insert the medical tool, for example according to the position of the polyp.

Second working channel 640b may be formed as an essentially cylindrical channel located within secondary distal channeling section 604b along the long dimension of the endoscope and placed in parallel to secondary distal channeling section 604b. Other configurations may also be possible. First and second working channels may be the same or different in shape and size.

Second working channel 640b may be configured to improve the performance of the endoscope (particularly, the colonoscope). Current colonoscopes typically have one working channel, which opens at the front distal section of the colonoscope. Such front working channel is adapted for insertion of a surgical tool. The physician is required to perform all necessary medical procedures, such as biopsy, polyp removal and other procedures, via this one channel.

According to some embodiments of this invention, there is provided herein an endoscope (such as colonoscope) that includes (in a tip section thereof), in addition to a front camera and one or more side cameras, and in addition to a front working channel, also a second front working channel that is configured for insertion of a medical (such as a surgical) tool, optionally in addition to a medical tool inserted from the front working channel.

A second working channel, such as second working channel 640b allows greater flexibility to the endoscope operator and allow the insertion of medical tools in addition to (or instead of) the medical tools which may be inserted through working channel 640a.

This may significantly improve the performance of the endoscope and allow the endoscope operator to perform more complex medical procedures using two medical tools. Second working channel 640b provides the endoscope operator a better access to the object of interest and greater flexibility with operating the medical tools while at the same time viewing the procedure by the front pointing camera 116a (FIG. 1). This substantially increases the performance of the endoscope. Moreover, the two front working channels may be used simultaneously for medical procedures. An example of such procedure may include surgery that requires stitching which can more easily be performed using two tools from two channels.

Another example of simultaneous usage of two working channels may include cleaning of the colon. A common problem exists when physicians find out that the patient's colon is not sufficiently clean. In such cases, the physician can try to clean the colon part using the "jet" exiting from the front part of the tip and in bad cases the physician is forced to send the patient home and reschedule his/her appointment. According to embodiments of the invention, the two channels can be used simultaneously for cleaning. For example, a cleaning fluid (such as water or water with air) may be inserted through one working channel and suctioned out from a second working channel. This may allow a better cleaning procedure that may solve or mitigate the problem of less efficient colonoscopies due to a non-cleaned colon.

In addition, a colonoscopy performed using a colonoscope according to embodiments of the invention may save the need of a cleaning procedure, currently performed by the patient him/herself, prior to colonoscopy.

Distal fluid channeling section 604 may further include a jet fluid channel 644 which may be configured for providing high pressure jet of fluid such as water or saline for cleaning the walls of the body cavity (such as the colon) and optionally for suction. Distal fluid channeling section 604 may further include a injector channel pathway 647 of injector channel 646, which may be used for blending two fluids (like air and water) and convey the fluid blend into injector channel 646 which may be configured to inject the fluid blend and wash contaminants such as blood, feces and other debris from front optical assembly 256a (FIG. 1) of front-pointing camera 116a (FIG. 1).

Proximal fluid channeling section 602 of fluid channeling component 600 may include side injector channels 666a and 666b, which may be connected to side injectors opening 266a and 266b (FIG. 1) respectively.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. An endoscope assembly, the assembly comprising:
    a substantially cylindrical fluid channeling component having a length and a height, the fluid channeling component having, along said height, a first fraction and a second fraction, wherein:
    the first fraction extends outward along the length of the fluid channeling component, and comprises a housing that has encased therein a working channel extending along the length of said fluid channeling component, and the second fraction is a void;
    an electrical assembly configured to fit within said second fraction, wherein the electrical assembly comprises an integrated circuit board having mounted thereon a front-pointing camera, a first side-pointing camera, and a second side-pointing camera; and
    two front illuminators positioned adjacent the front-pointing camera, two first side illuminators positioned adjacent the first side-pointing camera, and two second side illuminators positioned adjacent the second side-pointing camera;
    a tip cover section configured to be removably attachable to said fluid channeling component and configured to receive said electrical assembly, wherein the tip section comprises a front working channel configured to mate to said working channel of the fluid channeling component and provide a contiguous pathway for receiving a medical tool, optical windows configured to mate to said two front illuminators, optical windows positioned along a first side of the tip section and configured to mate to said two first side illuminators, and optical windows positioned along a second side of the tip section and configured to mate to said two second side illuminators.

2. The assembly according to claim 1, further comprising at least one front fluid injector configured for cleaning at least one of said front-pointing camera and at least one of said front illuminators.

3. The assembly according to claim 1, further comprising at least one side fluid injector configured for cleaning at least one of said side-pointing cameras and at least one of said side illuminators.

4. The assembly according to claim 1, further comprising a pathway fluid injector for inflating and/or cleaning a body cavity into which the endoscope is inserted.

5. The assembly according to claim 1, wherein said side-pointing cameras are directed to opposing sides.

6. The assembly according to claim 1, wherein each of said side-pointing cameras are essentially perpendicular to a surface of said front camera.

7. The assembly according to claim 1, wherein at least one of the side-pointing cameras forms an obtuse angle with said front camera.

8. The assembly according to claim 1, wherein at least one of the side-pointing cameras forms an acute angle with said front-pointing camera.

9. The assembly according to claim 1, wherein at least one of said front and side illuminators comprises at least one discrete illuminator.

10. The assembly according to claim 9, wherein each of said front and side illuminators comprises a light-emitting diode (LED).

11. The assembly according to claim 1, wherein at least one of said front and side illuminators is configured to emit white light.

12. The assembly according to claim 1, wherein at least one of said front and side illuminators is configured to emit ultra-violet light.

13. The assembly according to claim 1, wherein at least one of said front and side illuminators is configured to emit infra-red light.

14. The assembly according to claim 1, wherein at least one of said front and side illuminators is configured to emit near-infrared light.

15. The assembly according to claim 1, wherein said front and side illuminators are configured to emit light in different wavelengths.

16. The assembly according to claim 1, wherein each of said front-pointing and side-pointing cameras comprises an image sensor.

17. The assembly according to claim 1 further comprising a front fluid injector and a side fluid injectors connected to a same fluid supply channel.

18. The assembly according to claim 1, wherein said endoscope is a colonoscope.

19. The assembly according to claim 1, wherein said endoscope is a flexible endoscope.

20. The assembly according to claim 1, wherein said endoscope is a gastroscope.

21. The assembly according to claim 1, wherein fields of view of said front-pointing and side-pointing cameras are at least partially overlapping.

22. The assembly according to claim 1, wherein said at least one of said front and side-pointing cameras comprises a lens assembly providing a field of view of 90 degrees or more.

23. The assembly according to claim 1, wherein said at least one of said front and side-pointing cameras comprises a lens assembly providing a field of view of 120 degrees or more.

24. The assembly according to claim 1, wherein said at least one of said front and side-pointing cameras comprises a lens assembly providing a focal length of approximately 3-100 millimeters.

\* \* \* \* \*